United States Patent [19]
Hitzman

[11] 3,965,985
[45] June 29, 1976

[54] MICROBIAL SYNTHESIS FROM ALDEHYDE CONTAINING HYDROCARBON DERIVED PRODUCTS

[75] Inventor: Donald O. Hitzman, Bartlesville, Okla.

[73] Assignee: Phillips Petroleum Company, Bartlesville, Okla.

[22] Filed: Oct. 18, 1974

[21] Appl. No.: 515,873

Related U.S. Application Data

[60] Division of Ser. No. 366,563, June 4, 1973, Pat. No. 3,856,774, which is a continuation of Ser. No. 167,177, July 29, 1971, abandoned, which is a division of Ser. No. 751,926, Aug. 12, 1968, Pat. No. 3,642,578.

[52] U.S. Cl. .............................. 166/275; 166/246; 166/294; 175/66; 195/31 P
[51] Int. Cl.$^2$ ........................................ E21B 43/16
[58] Field of Search ................ 195/3, 12, 49, 31 P, 195/28 R, 50, 51; 260/209 R; 166/275, 294, 295; 175/65, 66; 252/8.5 C, 8.55

[56] References Cited
UNITED STATES PATENTS

| | | | |
|---|---|---|---|
| 3,208,518 | 9/1965 | Patton | 166/246 |
| 3,208,524 | 9/1965 | Horner et al. | 166/294 |
| 3,243,000 | 3/1966 | Patton et al. | 175/65 |
| 3,282,916 | 11/1966 | Jansen | 195/31 P X |
| 3,293,145 | 12/1966 | Leavitt et al. | 195/28 R X |
| 3,320,136 | 5/1967 | Zajic | 195/28 R X |
| 3,406,114 | 10/1968 | Goren | 195/31 P X |
| 3,436,311 | 4/1969 | Ferguson et al. | 195/31 P X |
| 3,474,001 | 10/1969 | Leavitt | 195/28 R |
| 3,591,455 | 7/1971 | Oppermann | 195/28 R |
| 3,642,575 | 2/1972 | Tanaka et al. | 195/28 R |

Primary Examiner—A. Louis Monacell
Assistant Examiner—R. B. Penland

[57] ABSTRACT

Proteins, amino acids, gums, and other valuable fermentation products are efficiently biosynthesized from hydrocarbon derived feedstocks containing aldehydes which have been admixed with a nitrogen-containing compound before being passed to a fermentor.

15 Claims, 1 Drawing Figure

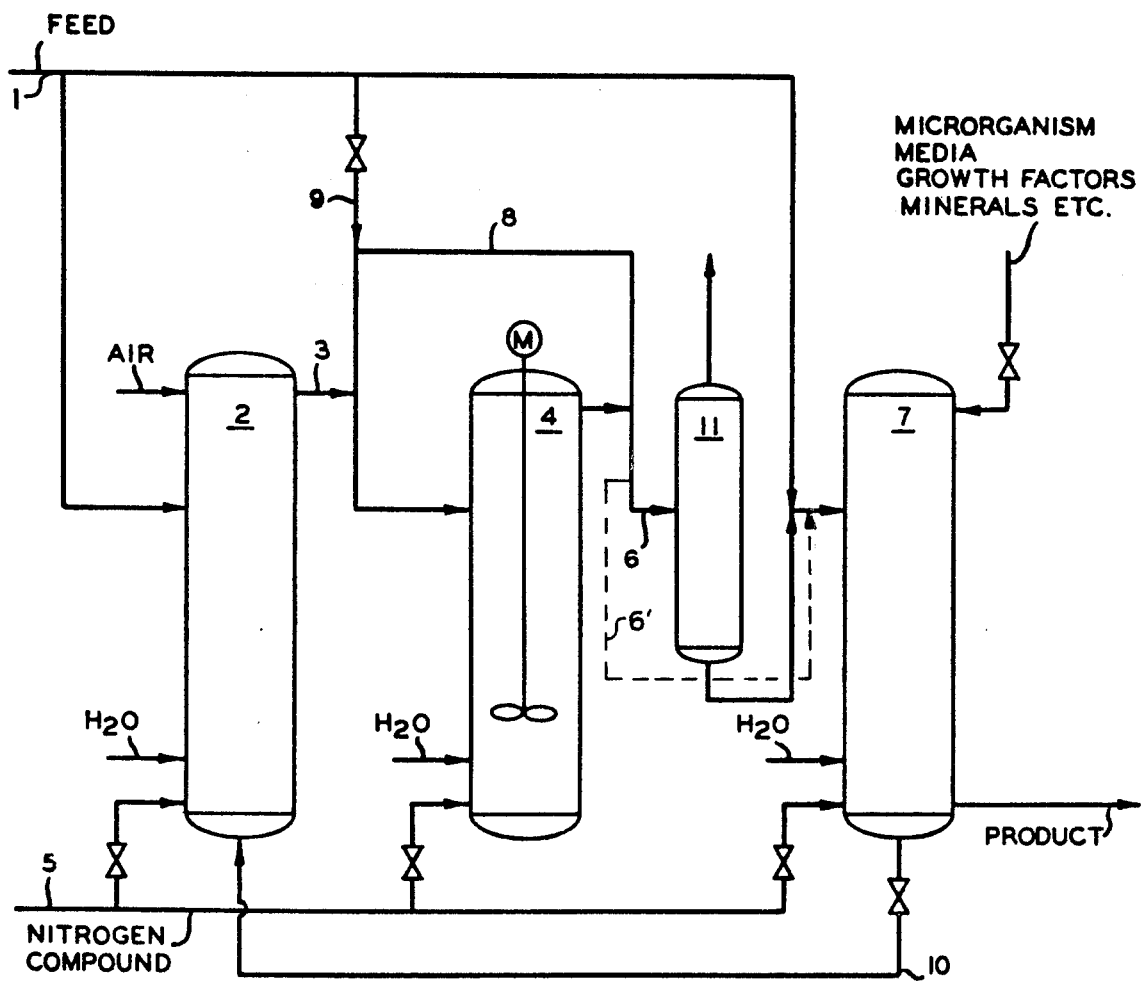

MICROBIAL SYNTHESIS FROM ALDEHYDE CONTAINING HYDROCARBON DERIVED PRODUCTS

This is a divisional application of Ser. No. 366,563, filed June 4, 1973, now U.S. Pat. No. 3,856,774, patented Dec. 24, 1974; which is a continuation application of Ser. No. 167,177, filed July 29, 1971, now abandoned; which is a divisional application of Ser. No. 751,926, filed Aug. 12, 1968, now U.S. Pat. No. 3,642,578, issued Feb. 15, 1972.

This invention relates to a process of microbial conversion of hydrocarbon derived products to proteins, amino acids, gums, and other valuable products. In another embodiment, this invention relates to a method of utilizing oxidized derivatives of methane, such as formaldehyde and methanol, as the feedstock for microbial fermentation. This invention further relates to unique combination of integrated procedures for microbial synthesis of cellular products.

It is known that microorganisms have the ability to manufacture edible protein by the fermentation of hydrocarbons.

There is avid interest in this field for hydrocarbons represent one of the greatest sources of raw materials suitable as potential foodstuffs that can be employed to meet a continuing critical world shortage of edible protein.

Large-scale protein synthesis has not developed to the high degree of efficiency wherein high yields of protein are obtained by economical procedures.

The conversion of methane and n-paraffins to edible protein is recognized, but protein so manufactured is known to be frequently contaminated by oil and other deleterious hydrocarbons often resulting in decreased cellular yields and high production cost necessitated by extensive separating, centrifuging, and washing procedures in order to achieve an efficacious product free from aromatic and carcinogenic contamination and hence, suitable as foodstuffs.

Most oxidation products of methane, such as formaldehyde, are considered biocidal in nature and deleterious to the microbial fermentation process. Commercial methanol, an oxidation product of methane, which can be used as a hydrocarbon derived feedstock often contains deleterious quantities of formaldehyde and consequently inhibits or decreases microbial productivity.

It is known that some microorganisms are capable of incorporating and oxidizing formaldehyde but heretofore formaldehyde, even at low concentrations, was considered biocidal by those skilled in the art.

In accordance with the instant invention, it has surprisingly been discovered that hydrocarbon derived products containing substantial amounts of aldehydes, even formaldehyde, whose toxicity to microorganisms is well documented, can be successfully empolyed as a nutritional feedstock for microbial fermentation when they have been admixed with a nitrogen-containing compound before being passed to a fermentor.

According to one embodiment of this invention, a procedure has been discovered for utilizing products formed by the oxidation of hydrocarbons. Conversion procedures for obtaining the hydrocarbon derived product, such as the Fischer-Tropsch synthesis Topsoe, ICI or other chemical synthesis processes, can be employed to produce the microbial feedstock. High quality protein can also be economically and abundantly manufactured by the oxidation and fermentation of widely available hydrocarbon sources such as natural gas, petroleum, naphtha, coal, peat, asphalt and the like.

In another embodiment of the invention, hydrocarbons are oxidized and contacted with an aldehyde reactive nitrogen-containing compound, and the water-soluble mixture formed thereby is fed to a fermentor for microbial fermentation resulting in an uncontaminated microbial production product suitable as a protein food source.

In still another embodiment of this invention, substantial quantities of protein are economically synthesized by an integrated process wherein a hydrocarbon is oxidized, the resultant mixture water washed, the aqueous solution is contacted with ammonia, and the water-soluble mixture is separated and fed directly into a fermentor.

It is an object of this invention to provide protein, amino acids, and other valuable microbial production products to alleviate the continual world shortage of foodstuffs. It is an object of this invention to provide an improved process for the utilization of methane derivatives including methanol as the microbial feedstock. It is an object of this invention to produce gum fermentation products suitable as adhesives, water viscosifiers, oil recovery adjuncts, etc. It is another object of this invention to provide an economical procedure whereby feedstocks containing aldehydes can be effectively fed directly into a fermentor for cellular production. Other objects, advantages, embodiments of this invention will be evident to those skilled in the art from the disclosure and the discussion herein set forth.

FIG. 1 is a diagram of a schematic flow sheet demonstrating implementation of some embodiments of our invention.

Unfortunately, according to the literature, in the direct oxidation of one of the most abundant hydrocarbon sources available, methane, to the oxidized hydrocarbon derivative methanol, formaldehyde is also produced. The concentration of formaldehyde, futhermore, becomes biocidal when conversion rates of methanol that would lend themselves to efficient economic production, are employed. Utilization of pure methanol is often economically prohibitive.

This tremendous obstacle to the feasibility of efficiently and economically manufacturing synthetic high grades of protein has now been eliminated. A process has now been discovered whereby nutrient hydrocarbon derived feedstocks containing deleterious quantities of aldehydes, ketones, carboxylic acids, and the like can effectively be incorporated in the fermentation process by reacting the aldehyde containing feed with nitrogen containing compounds before the resultant mixture is fed to a fermentor. In accordance with this method, aldehydes such as formaldehyde or acetaldehyde are not only tendered innocuous but they can be employed as the sole carbon and energy source for microbial production of protein.

A hydrocarbon, such as methane, can now be oxidized to methanol and formaldehyde without using expensive carefully controlled oxidation reaction steps to prevent the formation of deleterious quantities of aldehydes. Time and expense are consequently, jointly conserved. It is to be understood that when the term "hydrocarbon derived" is used, we are referring to compounds that can be produced from hydrocarbon such as by oxidation or that can be obtained by other known methods.

Our process has enhanced desirability because higher maximum efficiency of microbial activity is achieved. The hydrocarbon-derived feedstock that has previously been partially oxidized and rendered essentially free of oil and other undesirable contaminants permits maximum efficiency and conservation of microbial activity.

Examples of those products which can be employed as microbial feedstocks according to this invention include the water-soluble aliphatic alcohols, ketones, aldehydes, carboxylic acids, ethers, and polyols, preferably containing as many as 10 carbon atoms. Some illustrative examples include: methanol, ethanol, propanol, butanol, pentanol, hexanol, 1,7-heptandiol, 2-heptanol, 2-methyl-4pentanol, pentanoic acid, 2-methylbutanoic acid, 2-pentanol, 2-methyl-4-butanol, 2-methyl-3butanol, 2-butanol, 2-methyl-1-propanol, 2-methyl-2-propanol, 2-propanol, formic acid, acetic acid, propanoic acid, formaldehyde, acetaldehyde, propanal, butanal, 2-methylpropanal, butanoic acid, 2-methylpropanoic acid, pentanoic acid, glutaric acid, hexanoic acid, 2-methylpentanoic acid, heptandioic acid, heptanoic acid, 4-heptanone, 2-heptanone, octanoic acid, 2-ethylhexanoic acid, glycerine, ethylene glycol, propylene glycol, 2-propanone, 2-butanone, diethyl ether, methyl ethyl ether, dimethyl ether, di-n-propyl ether, n-propyl isopropyl ether, and the like.

Our discovery comprises a process wherein the microbial feed is contacted with nitrogen-containing compounds that are reactive with aldehydes. The aldehydes modified by or in the presence of the nitrogen-containing compound become effective nutrients and the resultant mixture can be fed directly into a fermentor as a carbon and hydrogen nutrient feedstock for cellular production by the microorganisms under conditions suitable for fermentation. It is preferred that only the water-soluble products of the resultant mixture be fed to the fermentor.

Efficient utilization of almost any hydrocarbon or carbonaceous raw material such as natural gas, petroleum, naphtha, coal, peat, asphalt and the like; and conversion thereof via oxidation and subsequent microbial conversion to microbial production products essentially free of oil and other hydrocarbon contaminants is obtained with an excellent fermentation productivity rate according to this process.

Ethylene can be converted to acetaldehyde and the acetaldehyde and other oxidized water-soluble products resulting from the oxidation process can be used as a feedstock after they have been admixed with ammonia or nitrogen-containing compounds such as urea. Since nitrogen is required for cellular growth, both to neutralize the acids produced and to provide nitrogen for protein synthesis, our method of admixing a nitrogen-containing compound such as ammonia or urea prior to the fermentation effectively accomplishes the foregoing in addition to rendering the feedstock nontoxic if aldehydes are present. Carbon dioxide produced by microbial metabolism in the fermentation process can be incorporated into the whole process by recycling and converting it for use in a Fischer-Tropsch synthesis, or other chemical synthesis processes known to the art, as described in Kirk-Othmer, Encyclopedia of Chemical Technology, 2nd Edition, Vol. 13, pp 382–383, and Vol. 4, pp 446–480, and consequently promoting increased efficiency.

Other synthetic means of producing the oxygenated hydrocarbon feed source are likewise familiar to those knowledgeable in the art and can be produced such as according to the well-known oxo process where a suitable olefin in hydroformylated with carbon monoxide and hydrogen to from aldehydes and alcohols and the Topsoe and ICI synthesis as described in Oil and Gas Journal, Aug. 14, 1967, p 82, and Feb. 12, 1968, p 106–109.

FIG. 1 is exeamplary of one preferred embodiment of this novel process and represents a schematic flow sheet to aid in the mastery and implementation of this invention. It is not, however, nor are the materials used therein, to be construed or interpreted as a limitation on the scope thereof.

In one embodiment of this invention, a crude or impure hydrocarbon or carbonaceous feed source 1, can be oxidized in the vessel 2. The oxidized hydrocarbon derivative can be fed via conduit 3 to the vessel 4, where it can be admixed with the nitrogen-containing compound from source 5. The reaction mixture thereof can be directly fed via conduit 6' into the fermentor 7 omitting or by-passing vessel 11, as the microbial feedstock for cellular production. The discretionary employment of vessel 11 will be discussed hereinafter.

In another variation, an aldehyde-containing feed from said source 1 can be fed via conduit 9 to said vessel 4 where it can be admixed with said nitrogen-containing compound from said source 5, and the resulting mixture passed via said conduit 6' directly to said fermentor 7.

Other modifications, such as employing said vessel 2 for the Fischer-Tropsch synthesis of oxygenated hydrocarbon derivatives and feeding the said oxygenated hydrocarbon via said conduit 3 to said vessel 4 where it is admixed with said nitrogen-containing compound from said source 5, and the resulting mixture passed via said conduit 6' directly to said fermentor 7, and the recycling of carbon dioxide from said fermentor 7 via conduit 10 back to said vessel 2 is contemplated.

In still another modification, an oxygenated hydrocarbon from source 1 can be fed to said vessel 12 and the nitrogen-containing compound from said source 5 admixed therewith and the resultant mixture fed via conduit 3 to said vessel 4, water washed therein and the water-soluble products thereof fed via said conduit 6 and through the water separation vessel 11 to said fermentor as a water-soluble oxygenated hydrocarbon feed.

It is believed probable that the conversion of biodeleterious aldehydes, such as formaldehyde, to products such as hexamethylenetetramine and the like is largely responsible for the microbial suitability of these materials as feedstocks.

It is a critical embodiment of our invention that the nitrogen-containing compounds that are reactive with aldehydes be admixed with the oxygenated hydrocarbon feedstock containing aldehydes before introduction of the resultant mixture to the fermentor.

Illustrative examples of suitable nitrogen-containing compounds which can be employed include ammonia, ammonium hydroxide, ammonium sulfate, ammonium nitrate, ammonium phosphate, acetonitrile, urea, guanidine, uric acid, and the like. Ammonia or ammonium compounds are presently preferred.

Sufficient amounts of the nitrogen-containing compound should be added to render innocuous a substantial amount of the deleterious material in the feedstock. Normally, from about 0.01 to 10 mol equivalents of said nitrogen-containing compound should be provided for each mol of aldehyde.

The fermentation process is carried out according to the conditions generally known in the art to support microbial fermentation. Generally, temperatures in the range of about 15°C to about 60°C and pressures in the range of about 0.1 to 100 atmospheres are employed. Normally pressures in the range of about 1 to 30 atmospheres are used.

One of the most important limitations to increased cell production is the dissolved oxygen level in the fermentor. The dissolved oxygen can be increased by running the fermentor under increased pressures. Pressures of about 0.1 to 50 atmospheres gage are usually employed. For illustration purposes, the methanol urea solution can be fed to a reactor using 8 psig air pressure. The dissolved oxygen level in the fermentor is consequently increased compared to atmospheric pressure and more cells can be grown in a shorter period of time using identically sized equipment. In addition, higher temperatures can be maintained because at high pressures the microorganisms can withstand higher temperatures; consequently, cooling expense is reduced. The increased pressure also aids in the recovery of metabolic products by supplying a driving force for filtration or drum drying. By suddenly releasing the pressure of the fermentor, cells can be ruptured, thus releasing cellular components and consequently, a product of enhanced purity can be harvested. The sudden pressure release also volatilizes any volatile impurities present and enhances the overall efficacy of the process.

Sufficient water is present in the fermentation procedure to provide for the particular requirements of the microorganisms employed. Generally, any microorganism which is able to utilize oxygenated hydrocarbon feeds can be empoloyed. Suitable hydrocarbon utilizing bacteria can be cultured and developed as follows.

A soil sample is secured from below the ground surface from any desired plot. Samples of soil taken over a hydrocarbon bearing formation will generally contain more hydrocarbon consuming microorganisms than samples of soil taken over a non-hydrocarbon bearing area. It is preferred that the soil sample be taken at a sufficient depth below the surface of the ground to avoid surface contamination. Depths ranging from six inches to three feet are generally preferred, with depths from two to three feet being more preferred. When securing the samples, care should be taken so that the soil sample be a sample of relatively undisturbed soil at the desired depth. A convenient method of sampling is to dig a hole with the aid of an ordinary post hole digger to approximately the desired depth; then, by use of a hand auger, take a sample of undisturbed soil from the site of the hole at the desired depth.

A 200 g sample of soil obtained accordingly is blended for approximately 1 minute with 1000 ml of a sterile medium having the following composition:

Mineral Medium No. 1

| | |
|---|---|
| $H_2O$ | 1000 g |
| $MgSO_4$ | 0.1 g |
| $K_2HPO_4$ | 0.5 g |
| $CaSO_4$ | 0.1 g |
| $NH_4NO_3$ | 1.0 g |

The pH of the soil suspension is then adjusted to 7 with any non-deleterious base while the suspension is agitated. One ml of the soil suspension is then added to 100 ml of the said sterile mineral medium to give a 1 to 100 dilution soil suspension. One ml of the 1 to 100 dilution is then added to 100 ml of the mineral medium to give a 1 to 10,000 dilution soil suspension. The 1 to 10,000 soil suspension is then mixed with suffieient methanol to yield a 5 volume percent mixture. The cultures are then incubated for 6 days at about 37°C, after which streaks are made on Petri dishes containing agar medium prepared using the following recipe:

| | |
|---|---|
| $NH_4NO_3$ | 1.0 g |
| $MgSO_4$ | 0.1 g |
| $K_2HPO_4$ | 0.5 g |
| $CaSO_4$ | 0.1 g |
| Agar | 15.0 g |
| Distilled $H_2O$ | 1000 g |
| Sufficient methanol to give 1.5 vol. % methanol. | |

The Petri dishes are incubated for 6 days at about 37°C. Viable colonies are restreaked on other Petri dishes as before to purify the colonies.

Single colonies are then transported to mediums comprised according to the recipe for Mineral Medium No. 1 and containing sufficient methanol to comprise 1.5 volume percent of the total medium.

As will be evident to those skilled in the art various modifications of the mineral growth media can be employed thereby resulting in the propagation of various microorganisms.

The particular microorganism employed in this process is not critical and we have cultured and used many that are suitable for employment according to this invention. Exemplary of said microorganisms are *Pseudomonas methanica*, which has been assigned the numerical designation NRRL B-3449 by the Northern Utilization Research and Development Division, Peoria, Illinois, *Pseudomonas fluorescens*, numerical designation NRRL B-3452, *Methanomonas methanica*, numerical designation NRRL B-3450, *Methanomonas methanooxidans*, numerical designation NRRL B-3451, *Arthobacter parafficum*, numerical designation NRRL B-3452, and *Corynebacterium simplex*, numerical designation NRRL B-3454. The *Pseudomonas* sp. microorganisms were employed through the exemplary runs of our disclosure. Bacillus, Mycobacterium, Actinomyces, and Nocardia genuses are other illustrate examples of bacteria which have been tested and found to be suitable. Other examples of bacteria include the genuses: Micrococcus; Rhodobacillus; Chromatium; Nitrosomonas; Serratia; Nitrobacter; Rhizobium; Azotobacter; Aerobacter; Escherichia; Streptococcus; Bactrillum; Clostridium; and Corynebacterium. Other suitable classes of microorganisms include the yeasts, molds, fungi, and the like. Combinations of microorganisms can also be employed.

Suitable minerals, growth factors, vitamins, and the like are generally added in amounts sufficient to provide for the particular needs of the microorganisms utilized.

Mineral and growth factors, and the like, for the microorganisms which are employed vary according to the particular requirements of the microorganisms and are generally known to those skilled in the art or are readily determined by those so skilled.

Further addition of nitrogen compounds can be added to the fermentor, such as urea, or ammonia, if desired. The ammonium ions or nitrogen-containing compound charged to the oxidized hydrocarbon feedstocks of our process are normally a sufficient source of nitrogen, however.

Upon completion of the desired degree of fermentation, the microbial fermentation products can be separated by any means known to the art such as centrifugation, filtration, solvent extraction, stripping of volatiles, heating, and the like.

We have discovered that the addition of polar organic solvents such as acetone, ethanol, or methanol, after the fermentation has been completed was surprisingly effectual in precipitating the cells, polymeric gums, and production products from the media. An immediate precipitate was formed following the addition of excess polar organic solvent and the tightly bound cellular mass could be removed by mechanical means leaving a clear solution from which the solvent could be recovered and recycled.

It is a preferred effect of this invention to produce high quality nutritionally balanced protein materials suitable as foodstuffs. In another embodiment valuable porducts such as gums, vitamins, amino acids, growth factors, and the like can be produced.

We have discovered that abnormally high quantities of tryptophane, lysine, leucine, threonine, valine, alanine, and glutamic acid which are necessary supplements to deficient food can be synthesized according to Example I hereinafter reported by those aforementioned numerically designated nicroorganisms using a methanol-formaldehyde-ammonium hydroxide feedstock in the mineral salt media. These microorganisms grow in a continuous aerobic fermentation process and use this feedstock as both the carbon and nitrogen source and produce the water-soluble amino acids tryptophane, lysine, threonine, valine, alanine, and glutamic acid in the media. According to this embodiment, the microbial cells are recovered and sold as protein and the exhausted culture media is extracted and the amino acids recovered. Identification by paper chromatography establishes that when these aforedesignated microorganisms are grown on a methanol-formaldehyde-ammonium hydroxide feedstock, essentially these seven said amino acids are produced in abnormally high concentrations and excreted into the media, consequently providing a dual product.

*Pseudomonas methanica* was particularly high in the production of tryptophane, lysine, and threonine; *Pseudomonas fluorescens* in the production of lysine, threonine, leucine, tryptophane and valine; and *Corynebacterium simplex* in the production of leucine, lysine, threonine, tryptophane and alanine.

Exemplary of our disclosure and not to be intended as a limitation on the scope or the materials employed therein, the following examples are given.

EXAMPLE I

A 14 liter New Brunswick stirred fermentor suitably rigged for continuous fermentation and temperature controlled in the range of 32°–40°C, was charged with 7 liters suitable base medium[1] and with 500 cc of the aforesaid inoculum of *Pseudomonas* sp. (*Pseudomonas methanica* NRRL B-3449). Materials were charged to the reactor and effluent removed until the bacteria had reached an exponential rate of growth and a steady state had been reached. The following date illustrate steady-state fermentor operation (47–70 hours from start-up).

| Run 1 | |
|---|---|
| Conditions During Run | |
| Base Medium[1] | BH6[1] |
| Air Input | 10 liters/min |
| Stirrer | 1000 rpm |
| Growth Factors | none |
| Feed Rates | |
| Methanol: Formaldehyde Product[2] | 0.1452 liter/hr |
| NH$_4$OH (22–26% NH$_3$)[3] | 0.0291 liter/hr |
| Base Medium[1] | 1.200 liters/hr |
| Trace Minerals[4] | 0.016 liter/hr |
| Total Feed Rate | 1.3708 liters/hr |
| Steady State Fermentor Volume | 3.5 liters |
| Alcohol Content of Effluent | 1.13% |
| Based on These Conditions the Following Calculations Can Be Made: | |
| Retention Time in Fermentor | 2.55 hrs |
| Cell Concentration (dry weight) | 26.1 g/liter |
| Yield of Dried Cells/100 lbs of Methanol Consumed | 36.15 lbs |
| Yield of Dried Cells/100 lbs of[5] Methane Consumed | 72.3 lbs |
| Percent Protein of Cells[6] | 69.4% |
| Fermentor Productivity[7] | 10.23 g/liter/hr |

1. BH6 Base Medium has the following amounts of materials per liter of aqueous solution:

| | |
|---|---|
| KH$_2$PO$_4$ | 2.5 g |
| K$_2$HPO$_4$ | 2.5 g |
| (NH$_4$)$_2$SO$_4$ | 2.0 g |
| NaCl | 0.1 g |
| MgSO$_4$.7H$_2$O | 3.0 g |
| CaCl$_2$ | 0.04 g |
| Trace Minerals Soln[4] | 10 ml |

2. Methanol: Formaldehyde Product is comprised thus:
   14 parts Methanol
   1 part 37% aqueous HCHO
3. NH$_4$OH was admixed with the Methanol:Formaldehyde Product prior to passing to the fermentor.
4. Trace Mineral solution had the following amounts of the following compounds per liter of solution:

| | |
|---|---|
| CuSO$_4$.5H$_2$O | 0.06 g |
| KI | 0.08 g |
| FeCl$_3$.6H$_2$O | 4.80 g |
| MnSO$_4$.H$_2$O | 0.30 g |
| Na$_2$MoO$_4$.2H$_2$O | 0.20 g |
| ZnSO$_4$.7H$_2$O | 2.00 g |
| H$_3$BO$_3$ | 0.02 g |

5. Assuming 100% of theoretical conversion of CH$_4$ to CH$_3$OH if methane is first oxidized to methanol.
6. Percent protein equals percent N × 6.25.
7. Fermentor Productivity is in g of dried cells per liter of ferment per hour retention time in fermentor.

Example I clearly exemplifies the efficient productivity and high-cellular protein content achieved by our process.

EXAMPLE II

A run was effected as in Example I except that ammonium hydroxide was charged to the fermentor separately without prior admixing with the methanol:formaldehyde feedstock. The culture was eradicated and fermentation ceased.

Example II demonstrates the criticality of admixing the nitrogen-containing compound of this invention to the oxidized hydrocarbon containing feedstock prior to passing the feedstock to the fermentor.

EXAMPLE III

A 14 liter New Brunswick fermentor, suitably rigged for continuous fermentation and temperature controlled in the range of 32°–40°C, was operated at steady-state conditions employing a bacteria as in Example I, but according to the following conditions:

| Conditions During Run | | Run 3 | |
| --- | --- | --- | --- |
| Base Mediium | BH-5[8] | | |
| Air Input | | 8 liters/min | |
| Stirrer | | 1000 rpm | |
| Growth Factors | | None | |
| Feed Rates | | | |
|   Methanol | 15 vol parts | | |
|   HCHO (37 wt. % aqueous soln) | 1 vol part | 0.165 | liter/hr |
|   NH₄OH (25 wt. % aqueous soln) | 3 vol parts | | |
|   Base Medium | | 1.33 | liters/hr |
|   Trace Minerals | | 0.005 | liter/hr |
| Cell Concentration (dry weight) | | 23 | g/liter |
| (4) See Example I | | | |
| (8) BH-5 Base Medium is comprised as follows: | | | |
|   $KH_2PO_4$ | | 2.5 g/liter | |
|   $K_2HPO_4$ | | 2.5 g/liter | |
|   $(NH_4)_2SO_4$ | | 2.0 g/liter | |
|   NaCl | | 0.1 g/liter | |
|   $MgSO_4 \cdot 7H_2O$ | | 3.0 g/liter | |
|   $CaCl_2$ | | 0.02 g/liter | |
|   Trace Minerals Soln.[4] | | 3.75 ml/liter | |

The fermentor was monitored by means of: (a) pH of medium; (b) measurement of dissolved $O_2$ in medium; (c) gas chromatography of effluent, e.g., $CH_3OH$ and HCHO concentration; and (d) measurement of cell density of medium.

The input of methanol-formaldehyde-ammonium hydroxide and water mixture and base medium-trace mineral mixture was terminated. Immediately, a feed comprising 14 volume parts $CH_3OH$, 5 volume parts HCHO solution (37 wt. % aqueous solution), and 3 volume parts of $NH_4OH$ solution (25 wt. % aqueous solution) was charged to the fermentor on pH demand so as to maintain the pH at 6.5. A total of 50 cc of this mixture was charged to the fermentor. The monitored functions; e.g., pH = 6.5, uptake of $O_2$, absence of $CH_3OH$ or HCHO in effluent, and cell density of 23 g/liter remained constant. This demonstrated that the ferment was utilizing the higher HCHO concentration without difficulty.

When 50 cc of the above feed had been passed to the fermentor the feed was terminated. Immediately, a feed comprising 14 volume parts of $CH_3OH$, 5 volume parts of HCHO solution (37 wt. % aqueous solution), and 5 volume parts of $NH_4OH$ solution (25 wt. % aqueous solution) was charged to the fermentor on pH demand so as to maintain the pH at 6.5. A total of 160 cc of this mixture was charged to the fermentor. The monitored functions; e.g., pH = 6.5, uptake of $O_2$, absence of $CH_3OH$ or HCHO in effluent, and cell density of 23 g/liter remained constant. This demonstrated that the ferment was continuing to utilize the increased HCHO level of the feed wherein a higher level of $NH_4OH$ was employed.

When 160 cc of the above feed had been passed to the fermentor that feed was terminated. Immediately, a feed comprising 1 volume part of HCHO solution (37 wt. % aqueous solution) and 1 volume part of $NH_4OH$ solution (25 wt. % aqueous solution) was charged to the fermentor on pH demand so as to maintain the pH at 6.5. A total of 85 cc of this mixture was charged to the fermentor. The said monitored functions continued to remain constant.

When 85 cc of the above feed had been passed to the fermentor that feed was terminated. Immediately, a feed essentially comprising 37 wt. % HCHO aqueous solution was charged to the fermentor on pH demand so as to maintain the pH at 6.5. Almost immediately, the fermentation terminated as was determined by said monitored functions. The culture was eradicated before 25 cc of HCHO had passed to the fermentor.

Example III demonstrates the utilization of formaldehydes as a carbon energy source for cellular production by the microorganisms and further demonstrates the criticality of admixing the nitrogen-containing compound of this invention to the oxidized hydrocarbon containing feedstock prior to passing feedstock to the fermentor.

As before mentioned, we have discovered that in the fermentation process conducted substantially according to Example I, that considerable quantities of polymeric gums are produced in the product effluent. The gum can be recovered from the exhausted fermentation media by precipitation with polar organic solvents. It can then be dried to a powder for convenient storage and use.

Variations in the polymeric gum produced can be achieved by employing various of the aforementioned microorganisms or by variation of the medium composition. Yields of over 50 grams/liter dry weight of gums and cells have been achieved. These polymeric gums can be dissolved in water to form a solution which has a higher viscosity than pure water.

These gums can be used as water flood additives, as in the recovery of oil, by forming a solution with a desired viscosity equal that of the oil-in-place so that greater efficiency can be achieved in recovering said oil.

The gum can also be used as a drilling mud additive and as a water loss control agent. The gum material will increase the viscosity of a drilling mud to which it is added to the desired viscosity and will hold suspended solids. It has no sensitivity to salts and is compatible with other mud additives.

The polymeric gum can also be used as a selective plugging agent and viscosifier for oil formations, i.e., can be used to increase the viscosity of aqueous compositions used in the production of crude oil. The polymeric gum can be solubilized and injected into the formation at a pH below 10. In this pH range, the polymer penetrates to the desired zone or acts as a viscosifier. The pH can be adjusted to at least about 11–11.5 with a suitable basic material. At this pH, the polymeric gums are gelled and form a tough, stringy mass. Basic materials can thus be injected into the formation so that the gum sets up and forms a block. By manipulating the pH, the material can be made very viscous for more oil recovery or formed into a solid to provide a block. In other situations, it may be desirable to inject the caustic first and then follow it with the soluble gum, using a separate zone of water if necessary so premature setting up does not occur except in the zone of maximum water penetration. The material is protected from microbial degradation by the high pH. It is also possible to gel this gum material by adding to the material agents such as acetone, alcohols, and the like.

EXAMPLE IV

Viscosity of the product effluent containing said polymeric gums obtained from a fermentor operated typically as in Example I using *Pseudomonas fluorescens* NRRL B-3452 was measured in Brookfield LVT viscosimeter. The viscosities were 14,000 cps, 3800 cps, 1200 cps, 384 cps, and 247 cps at 0.3, 1.5, 6.0, 30, and 60 rpm (with a No. 2 spindle), respectively.

The product effluent was diluted with 3 parts of brine for each 1 part of effluent product, and the viscosity of the diluted mixture was measured in the Brookfield viscosimeter employing the No. 2 spindle. Viscosities of 100 cps, 40 cps, 20 cps, and 18 cps were observed at 1.5, 6.0, 30.0, and 60.0 rpm, respectively.

The foregoing tests effectively demonstrate that the polymeric gums produced according to this invention are useful as viscosifiers for water and water solutions.

EXAMPLE V

The product effluent containing said polymeric gums was diluted as above with 3 parts of Burbank brine, brine prepared to have the salt concentration found in the Burbank Oil Field of Oklahoma, for each part of product. Sand from formation outcrop known to serve as a reservoir for petroleum is packed into a pipe which is 72 inches in length. The sand is saturated with crude oil from the Burbank Field. The sand column is then heated to and maintained at the reservoir temperature of the Burbank Field, while Burbank brine is passed through the sand column until no more oil is eluted. Maintaining the temperature as before, the above 1:3 mixture of product effluent and Burbank brine is then passed through the sand, until no more oil is eluted. The total amount of additional oil produced by flooding with the product effluent and brine is equivalent to 7.8% of the pore volume of the sand column. Consequently, the foregoing tests demonstrate that flooding with polymeric gum product effluent and Burbank brine mixture resulted in an improved recovery of petroleum.

The polymeric gum has also been found to possess adhesive qualities and to be suitable as a replacement for casein or soy protein adhesives for compounding into paper coating agents.

EXAMPLE VI

The polymeric gum was employed to bond wood substrate and was discovered to possess an adhesive lap shear strength of 200 psi based upon ASTM Test No. D-1002-53T; consequently exemplifying the adhesive characteristics of this polymeric gum.

The concepts and products of this invention are applicable for a variety of useful purposes as indicated throughout our specification. Another valuable application of our process is to treat industrial waste and sewage water such as from petroleum and petrochemical operation that often contain aldehydes or other toxic contaminants with ammonia or ammonium hydroxide and subsequently subject the waste water to microbial action so as to render the waste material non-toxic. The ammonia treating step as taught by our invention permits microbial fermentation of the waste material by forming an amine compound which is easily degraded by the microorganism as well as providing favorable pH conditions therefor.

It is within the scope of this invention to vary the organism and fermentation environment to achieve maximum optimum yields of any of the many valuable products such as gums, vitamins, amino acids, growth factors, and the like that may be desired. Other modifications of this invention can be accomplished or followed as will be evident to those skilled in the art in light of the foregoing discussion and examples without departing from the spirit and scope thereof.

What is claimed is:

1. A method of water flooding which comprises diluting a polymeric gum possessing water viscosifying properties with water or brine to a suitable viscosity and injecting the resulting diluted polymeric gum into oil-bearing strata,
    wherein said polymeric gum is characterized as produced by process of microbiosynthesis as cellular production products from oxygenated hydrocarbon feedstock containing aldehydes in addition to other oxygenated hydrocarbons, which feedstock is characterized as formed by the oxidation of hydrocarbons, which process comprises the steps of:
    a. adding to said oxygenated hydrocarbon feedstock containing aldehydes at least one nitrogen-containing compound reactive with said aldehydes whereby said aldehydes are rendered substantially innocuous,
    b. culturing on said nitrogen-containing compound treated feedstock from said step (a) oxygenated hydrocarbon-utilizing microorganisms effective to produce polymeric gum under fermentation conditions, thereby producing said polymeric gum, and
    wherein said microorganism is selected from the genera consisting of Pseudomonas, Methanomonas, Arthobacter, Corynebacterium, Bacillus, Mycobacterium, Actinomyces, Nocardia, Micrococcus, Rhodobacillus, Chromatium, Serratia, Rhizobium, Aerobactor, Escherichia, and Streptococcus.

2. The process of claim 1 wherein said step (a) employs about 0.01 to 10 mole equivalent of said nitrogen-containing compound per mole of aldehyde present in said oxygenated hydrocarbon feedstock; said nitrogen-containing compound is ammonia, ammonium hydroxide, ammonium sulfate, or ammonium phosphate; and said fermentation is carried out at a temperature from about 15°C. to 30°C. at a pressure from about 0.1 to 100 atmospheres.

3. The process according to claim 2 wherein said oxygenated hydrocarbon feedstock comprises methanol and formaldehyde, and said microorganism is *Pseudomonas methanica* NRRL B-3449, *Pseudomonas fluorescens* NRRL B-3452, *Methanomonas methanica* NRRL B-3450, *Methanomonas methanooxidans* NRRL B-3451, *Arthobacter parafficum* NRRL B-3453, or *Corynebacterium simplex* NRRL B-3454.

4. The process of claim 3 wherein said microorganism is said *Pseudomonas fluorescens* NRRL B-3452.

5. The process of claim 3 wherein said microorganism is said *Pseudomonas methanica* NRRL B-3449.

6. A method of treating drilling mud which comprises mixing a polymeric gum product possessing water viscosifying qualities with drilling mud thereby adjusting the viscosity of said drilling mud,
   wherein said polymeric gum is characterized as produced by process of microbiosynthesis as cellular production products from oxygenated hydrocarbon feedstock containing aldehydes in addition to other oxygenated hydrocarbons, which feedstock is characterized as formed by the oxidation of hydrocarbons, which process comprises the steps of:
   a. adding to said oxygenated hydrocarbon feedstock containing aldehydes at least one nitrogen-containing compound reactive with said aldehydes whereby said aldehydes are rendered substantially innocuous,
   b. culturing on said nitrogen-containing compound treated feedstock from said step (a) oxygenated hydrocarbon-utilizing microorganisms effective to produce polymeric gum under fermentation conditions, thereby producing said polymeric gum, and
   wherein said microorganism is selected from the genera consisting of Pseudomonas, Methanomonas, Arthobacter, Corynebacterium, Bacillus, Mycobacterium, Actinomyces, Nocardia, Micrococcus, Rhodobacillus, Chromatium, Serratia, Rhizobium, Aerobacter, Escherichia, and Streptococcus.

7. The process of claim 6 wherein said step (a) employs about 0.01 to 10 mole equivalent of said nitrogen-containing compound per mole of aldehyde present in said oxygenated hydrocarbon feedstock; said nitrogen-containing compound is ammonia, ammonium hydroxide, ammonium sulfate or ammonium phosphate; and said fermentation is carried out at a temperature from about 15°C. to 60°C. at a pressure from about 0.1 to 100 atmospheres.

8. The method of claim 7 wherein said oxygenated feedstock comprises methanol and formaldehydes and said microorganism is *Pseudomonas methanica* NRRL B-3449, *Pseudomonas fluorescens* NRRL B-3452, *Methanomonas methanica* NRRL B-3450, *Methanomonas methanooxidans* NRRL B-3451, *Arthobacter parafficum* NRRL B-3453, or *Corynebacterium simplex* NRRL B-3454.

9. The method of claim 8 wherein said microorganism is said *Pseudomonas fluoroescens* NRRL B-3452.

10. The method of claim 8 wherein said microorganism is said *Pseudomonas methanica* NRRL B-3449.

11. A method of selective plugging of an oil-beaiang formation which comprises the steps of solubilizing at a pH below about 10 a polymeric gum possessing water viscosifying properties, injecting said solubilized polymeric gum into said formation, thereafter injecting an alkaline material into said formation sufficient to raise the pH of said solubilized polymeric gum in said formation, and thereby increasing the viscosity of said polymeric gum in said formation,
   wherein said polymeric gum is characterized as produced by a process of microbiosynthesis as cellular production products from oxygenated hydrocarbon feedstock containing aldehydes in addition to other oxygenated hydrocarbons, which feedstock is characterized as formed by the oxidation of hydrocarbons, which process comprises the steps of:
   a. adding to said oxygenated hydrocarbon feedstock containing aldehydes at least one nitrogen-containing compound reactive with said aldehydes whereby said aldehydes are rendered substantially innocuous,
   b. culturing on said nitrogen-containing compound treated feedstock from said step (a) oxygenated hydrocarbon-utilizing microorganisms effective to produce polymeric gum under fermentation conditions, thereby producing said polymeric gum, and
   wherein said microorganism is selected from the genera consisting of Pseudomonas, Methanomonas, Arthobacter, Corynebacterium, Bacillus, Mycobacterium. Actinomyces, Nocardia, Micrococcus, Rhodobacillus, Chromatium, Serratia, Rhizobium, Aerobacter, Escherichia, and Streptococcus.

12. The process of claim 11 wherein said step (a) employs about 0.01 to 10 mole equivalent of said nitrogen-containing compound per mole of aldehyde present in said oxygenated hydrocarbon feedstock; said nitrogen-containing compound is ammonia, ammonium hydroxide, ammonium sulfate, or ammonium phosphate; and said fermentation is carried out at a temperature from about 15°C. to 60°C. at a pressure from about 0.1 to 100 atmospheres.

13. The method of claim 12 wherein said oxygenated feedstock comprises methanol and formaldehyde, and said microorganism is *Pseudomonas methanica* NRRL B-3449, *Pseudomonas fluorescens* NRRL B-3452, *Methanomonas methanica* NRRL B-3450, *Methanomonas methanooxidans* NRRL B-3451, *Arthobacter parafficum* NRRL B-3453, or *Corynebacterium simplex* NRRL B-3454.

14. The method of claim 13 wherein said microorganism is said *Pseudomonas fluorescens* NRRL B-3452.

15. The method of claim 13 wherein said microorganism is said *Pseudomonas methanica* NRRL B-3449.

* * * * *

UNITED STATES PATENT AND TRADEMARK OFFICE
CERTIFICATE OF CORRECTION

PATENT NO. : 3,965,985
DATED : June 29, 1976
INVENTOR(S) : Donald O. Hitzman

It is certified that error appears in the above—identified patent and that said Letters Patent are hereby corrected as shown below:

Column 12, line 55, delete "30°C." and insert --- 60°C. ---; and

Column 13, line 49, delete "beaiang" and insert --- bearing ---.

Signed and Sealed this

Thirtieth Day of November 1976

[SEAL]

Attest:

RUTH C. MASON
*Attesting Officer*

C. MARSHALL DANN
*Commissioner of Patents and Trademarks*